United States Patent
Berckmans et al.

(10) Patent No.: US 10,239,958 B2
(45) Date of Patent: Mar. 26, 2019

(54) PROCESS FOR MODIFYING STARCHES

(71) Applicant: Cargill, Incorporated, Wayzata, MN (US)

(72) Inventors: Marc Berckmans, Brussels (BE); Jozef Victor Jean-Marie Coppin, Denderleeuw (BE); Stephane Jules Jerome Debon, Brussels (BE)

(73) Assignee: Cargill, Incorporated, Wayzata, MN (US)

(*) Notice: Subject to any disclaimer, the term of this patent is extended or adjusted under 35 U.S.C. 154(b) by 268 days.

(21) Appl. No.: 15/254,610

(22) Filed: Sep. 1, 2016

(65) Prior Publication Data

US 2017/0051079 A1 Feb. 23, 2017

Related U.S. Application Data (62) Division of application No. 13/639,202, filed as application No. PCT/EP2011/055454 on Apr. 7, 2011, now abandoned.

(30) Foreign Application Priority Data

Apr. 7, 2010 (EP) .................................. 10159277

(51) Int. Cl.
  *C08B 30/12* (2006.01)
  *C08B 30/16* (2006.01)
  (Continued)

(52) U.S. Cl.
  CPC ............. *C08B 30/12* (2013.01); *A23K 20/00* (2016.05); *A23K 20/10* (2016.05); *A23K 20/163* (2016.05);
  (Continued)

(58) Field of Classification Search
  None
  See application file for complete search history.

(56) References Cited

U.S. PATENT DOCUMENTS 4,280,851 A * 7/1981 Pitchon ................... C08B 30/16
                                                    127/28
4,469,524 A   9/1984 Assarsson et al.
(Continued)

FOREIGN PATENT DOCUMENTS

EP           0032296        7/1981
WO     WO 2005/047340        5/2005
(Continued)

OTHER PUBLICATIONS

European Search Report from corresponding European application EP 10159277, dated Aug. 27, 2010, 1 page.
(Continued)

*Primary Examiner* — Melvin C. Mayes
*Assistant Examiner* — Stefanie J Cohen (57) ABSTRACT

A process for modifying starch comprises atomising an aqueous slurry of non-pregelatinised starch into an internal chamber in a bi-fluid nozzle of a spray dryer and treating the atomized slurry, in the internal chamber, with superheated steam to cause partial gelatinisation of the starch. The aqueous slurry containing partially gelatinised starch is discharged through an outlet in the internal chamber into a reactor where the droplets containing the partially gelatinised starch are subjected to further treatment with superheated steam, resulting in the completion of the gelatinisation of the starch in the reactor. Also disclosed is a bi-fluid nozzle for use in spray drying starch which comprises a nozzle body, a nozzle cap and an internal chamber located between the nozzle body and the nozzle cap. The nozzle body comprises at least one atomiser, for connection to a supply of an aqueous starch slurry, for atomising the slurry (Continued)

into the internal chamber and it has at least one inlet, for connection to a supply of superheated steam under pressure, for introducing superheated steam under pressure into the internal chamber. The nozzle cap comprises at least one outlet from the internal chamber. The internal chamber also comprises an interchangeable spacer element with a length of from 10 to 60 mm enabling the length of the internal chamber to be changed. A pregelatinised starch and its use in foods, especially baby foods and infant formulas, feed, pharmaceuticals, cosmetics and personal care products are also disclosed.

8 Claims, 2 Drawing Sheets

(51) Int. Cl.
| | | |
|---|---|---|
| *A61K 8/73* | (2006.01) | |
| *A23L 29/212* | (2016.01) | |
| *A23K 20/10* | (2016.01) | |
| *A23K 20/163* | (2016.01) | |
| *A61Q 19/00* | (2006.01) | |
| *A61K 8/04* | (2006.01) | |
| *A23K 20/00* | (2016.01) | |

(52) U.S. Cl.
CPC ............ *A23L 29/212* (2016.08); *A61K 8/042* (2013.01); *A61K 8/732* (2013.01); *A61Q 19/00* (2013.01); *C08B 30/16* (2013.01); *A61K 2800/10* (2013.01)

(56) References Cited

U.S. PATENT DOCUMENTS

| | | |
|---|---|---|
| 6,099,871 A | 8/2000 | Martinez |
| 6,221,420 B1 | 4/2001 | Thomas et al. |
| 6,645,541 B2 * | 11/2003 | Morii ............... A23L 29/212 426/241 |
| 7,332,178 B2 | 2/2008 | Byard et al. |

FOREIGN PATENT DOCUMENTS

| | | |
|---|---|---|
| WO | WO 2009/013346 | 1/2009 |
| WO | WO 2011/124656 | 10/2011 |

OTHER PUBLICATIONS

Fennema, O., 1996, Food Chemistry, p. 193.
PCT International Search Report PCT/EP2011/055454, dated Jun. 22, 2011, 1 page.
File History of U.S. Appl. No. 13/639,202, filed Oct. 4, 2012.

* cited by examiner

PROCESS FOR MODIFYING STARCHES

This application is a divisional of U.S. application Ser. No. 13/639,202, filed Oct. 4, 2012, now abandoned, which is a national stage application of International Patent Application No. PCT/EP2011/055454, filed Apr. 7, 2011, which claims benefit or European Application No. EP 10159277.2, filed Apr. 7, 2010, each of which is incorporated by reference herein in its entirety for any purpose.

TECHNICAL FIELD

The present invention relates to a process for modifying starches by subjecting a non-pregelatinised starch to a superheated steam treatment. The invention, further, relates to pregelatinised starch products and, also, to a nozzle for a spray drying apparatus.

BACKGROUND OF THE INVENTION

When a starch has been pre-cooked, it can be used to thicken cold foods. Such a starch is referred to as a pregelatinised or instant starch. Otherwise, starch requires heat to cause it to thicken or "gelatinise". The actual temperature required to gelatinise starch in an excess of water depends on the type of starch. Pregelatinised starches are particularly widely used in convenience foods such as instant soups, instant sauces, instant gravies, instant beverages, salad dressing mixes and the like, in dairy foods, such as instant puddings and the like, in bakery foods, such as cake mixes, bakery creams and the like, and in instant baby and infant foods.

The terms "gelatinised" or "cooked" starch refers to swollen granules which have lost their polarisation crosses and which may or may not have lost their granular structure. The term "partially gelatinised" starch refers to partially swollen granules which have not yet completely lost their polarisation crosses. The thermal processes generally employed to prepare pregelatinised starches include roll drying, extrusion, high temperature heating in alcohol/water systems and spray cooking/drying. The physical properties of the pregelatinised starches, in particular the wettability, the dispersibility and peak viscosity in cold water, arc dependent on the process used to pregelatinise the starch.

Roll-dried and spray cooked/dried starches are the most widely used pregelatinised starches on the market. These starches generally have less thickening power and less gelling tendency than the corresponding granular starch upon gelatinisation. The loss in thickening and gelling potential is related to the partial destruction of the hydrated granular structure. Roll-dried starches typically have less thickening power compared to spray cooked/dried starches. From a thermodynamic perspective, both common processes, roll drying and spray cooking/drying, are also not very energy efficient. There is therefore a need for pregelatinised starches which have high thickening powers in cold liquids and which can be produced via a process that is energetically more efficient compared to roll drying and spray cooking/drying. The process of this invention provides such starches.

JP 61-280244 discloses the heat treatment of starch in the presence of superheated steam of temperatures between 105 and 350° C. for less than 5 minutes at gauge-pressures of less than 9 kg/cm$^2$.

WO 2009/013346 relates to a process for modifying starches comprising subjecting a non-pregelatinised starch to a superheated steam treatment.

EP-A-0032296 describes a process and an apparatus for cooking or gelatinising a material in an atomised state, so that there is obtained an easily dryable, uniform and finely-sized product. According to this document, the material which is to be cooked is injected through an atomisation aperture in a nozzle assembly to form a relatively finely-sized spray which is heated in the nozzle assembly to a temperature effective to cook or gelatinise the material in the nozzle assembly.

The process according to the present invention provides pregelatinised starch products with novel and superior functionalities compared to conventional pregelatinised starches.

SUMMARY OF THE INVENTION

The current invention relates to a process for modifying starches. The process comprises the steps:

a) supplying an aqueous slurry of non-pregelatinised starch to a bi-fluid nozzle of a spray dryer, wherein the bi-fluid nozzle has an internal chamber having at least one inlet for the aqueous slurry of non-pregelatinised starch, at least one inlet for the supply of superheated steam and at least one outlet;

b) atomising the aqueous slurry of non-pregelatinised starch into the internal chamber of the bi-fluid nozzle;

c) injecting superheated steam into the internal chamber of the bi-fluid nozzle whereby the atomised aqueous slurry of non-pregelatinised starch is heated by the superheated steam in the internal chamber to produce a slurry of partially gelatinised starch, wherein the temperature of the superheated steam at the at least one inlet into the internal chamber is in the range of 150° to 650° C., preferably 250° to 550° C., more preferably 350° to 450° C.;

d) discharging the partially gelatinised starch from the internal chamber through the at least one outlet into a reactor; and e) contacting the discharged slurry in the reactor with superheated steam to completely gelatinise the partially gelatinised starch in the discharged slurry and to dry the completely gelatinised starch to produce dry, particulate pregelatinised starch.

The process of the invention is particularly useful for the treatment of low amylose starches. Preferably, the starch used in the process of the invention has an amylase content of not greater than 35% by weight. More preferably, the starch will be a low amylose starch having an amylase content not greater than 10% by weight, preferably not greater than 5% by weight.

According to a particularly preferred embodiment, in step a) of the process of the present invention as defined above, the aqueous slurry of non-pregelatinised starch is supplied to a bi-fluid nozzle which comprises a nozzle body, a nozzle cap and an internal chamber located between the nozzle body and the nozzle cap, wherein the nozzle body comprises at least one atomiser which is connected to the supply of the aqueous slurry of non-pregelatinised starch for atomising the aqueous slurry of starch into the internal chamber, wherein the internal chamber has at least one inlet therein connected to a supply of superheated steam under pressure for introducing the superheated steam under pressure into the internal chamber and wherein the nozzle cap comprises at least one outlet from the internal chamber, said internal chamber also comprising a replaceable and/or interchangeable spacer element with a length of from 4 to 1000 mm enabling the length of the internal chamber to be changed.

The current invention further provides a hi-fluid nozzle for use in spray-drying starch which comprises a nozzle body, a nozzle cap and an internal chamber located between the nozzle body and the nozzle cap, wherein the nozzle body comprises at least one atomiser adapted to be connected to a supply of an aqueous slurry of starch for atomising the aqueous slurry of starch into the internal chamber, wherein the internal chamber has at least one inlet therein adapted to be connected to a supply of superheated steam under pressure for introducing superheated steam under pressure into the internal chamber and wherein the nozzle cap comprises at least one outlet from the internal chamber, characterised in that the internal chamber also comprises an interchangeable spacer clement with a length of from 4 to 1000 mm enabling the length of the internal chamber to be altered.

The present invention also provides a pregelatinised starch having in UDMSO, (9 volumes DMSO, 1 volume 6M urea) at a concentration of 8 mg/ml at 25° C. a ratio of apparent viscosity of said pregelatinised starch to the apparent viscosity of the corresponding parent non-pregelatinised starch of between 1.00 and 1.18 at 1 $s^{-1}$, and a normalised storage modulus G' (c/c*) of a 6% by weight aqueous dispersion of said starch at 30° C. of between 15 and 30 Pa.

Furthermore, the invention relates to the use of the starches according to the present invention in food, feed, cosmetics, pharmaceutical applications and personal care products.

DETAILED DESCRIPTION OF THE INVENTION

The term "superheated steam" in the present invention means steam (=gaseous water) heated to a temperature higher than the boiling point corresponding to its pressure. Superheated steam cannot, therefore, exist in contact with water or contain water, and it resembles a perfect gas. It is also called surcharged steam, anhydrous steam, and steam gas.

The term "internal chamber", as used herein, is the place within the nozzle where the partial reaction between the non-pregelatinised starch and the superheated steam takes place. This reaction is partial since, according to the process of the invention, the starch is partially, i.e. not completely, gelatinised in the internal chamber. The term “internal chamber” is not limited to a particular form of a chamber, i.e. the shape, size or configuration of the chamber. The chamber can, for example, be in the form of a tube. The “internal chamber” possesses at least one inlet for the superheated steam, is vented by at least one outlet provided in or by the nozzle cap and is provided with atomised starch slurry by at least one atomiser.

The term “continuous reaction” as used herein is intended to distinguish such a reactor from a batch-type reactor.

The non-pregelatinised starches can be derived from any native source, wherein the term “native” relates to the fact that said starch is found in nature. Unless specifically distinguished, references to starch in this description are meant to include their corresponding flours. The flours may also contain proteins, such as wheat gluten. Typical sources of the starches are cereals, tubers, root legumes, fruit starches and hybrid starches. Suitable sources include, but are not limited to, corn, pea, potato, sweet potato, sorghum, banana, barley, wheat, rice, sago, amaranth, tapioca, arrowroot, canna, and low amylose starches (containing no more than about 35% by weight, preferably no more than 10% by weight amylose, more preferably no more than 5%) or high amylose starches (containing at least about 40% by weight amylose). Also suitable are starches derived from a plant obtained by breeding techniques including crossbreeding, translocation, inversion, transformation or any other method of gene or chromosome engineering to include variations thereof. In addition, starch derived from a plant grown from artificial mutations and variations of the above generic composition, which may be produced by known standard methods of mutation breeding, arc also suitable herein. The starch used can be a modified starch, for instance a chemically-modified starch or a physically-modified starch. Examples of chemically-modified starches include without limitation, acetylated starches, hydroxyethylated and hydroxypropylated starches, inorganically esterified starches, cationic, anionic, oxidized starches, zwitterionic starches, starches modified by enzymes, and combinations thereof, provided that the starches are not pregelatinised. Examples of physically modified starches include thermally inhibited starches such as those disclosed, for example, in EP 1 038 882A. In one preferred embodiment of the process of the invention, the non-pregelatinised starch to be treated is a low amylose starch having an amylose content not greater than 35% by weight, preferably no more than 10% by weight, more preferably no more than 5% by weight. Alternative preferred embodiments are potato starch, tapioca starch, n-OSA (n-octenyl succinic anhydride) starch having an amylose content not greater than 35% by weight, preferably no more than 10% by weight, more preferably no more than 5% by weight. It is to be understood that mixtures of any of the above mentioned non-pregelatinised starches and/or flours are also within the scope of this invention.

According to the process of the current invention, the non-pregelatinised starch and/or flour is treated with superheated steam in an internal chamber of a hi-fluid nozzle. A hi-fluid nozzle, sometimes called a two-fluid nozzle, is constituted by a liquid inlet and a gas inlet wherein the liquid and gas converge in an internal chamber before being discharged from the nozzle. In the present invention, an aqueous slurry of non-pregelatinised starch or flour is atomised into the internal chamber of the nozzle in which is created a superheated steam environment in view of the supply, into the chamber, of superheated steam. The temperature of the superheated steam at the inlet into the internal chamber is crucial for obtaining a partially gelatinised starch having the desired properties. The temperature of the superheated steam at the inlet of the internal chamber is in the range of 150° to 650° C., preferably 200° to 550° C., and more preferably 230° to 450° C. Further interesting results are obtained by running the process, such that the temperature of the superheated steam at the inlet of the internal chamber is 200° C., 205° C., or 230° C. to 250° C.

Typically, the non-pregelatinised starch will be in the form of an aqueous starch slurry having a pH of from 2 to 11, preferably 2 to 10.5, more preferably 2 to 10, even more preferably 2 to 9, yet more preferably from 3 to 8 and most preferably from 4 to 8.

The superheated steam is injected into the internal chamber and thereby displaces the air or other gas present in the internal chamber. Generally, the superheated steam is blown through the internal chamber before the reaction of non-pregelatinised starch with superheated steam until the air or other gas has been displaced. The absence of air in the internal chamber makes the process according to the present invention explosion-proof. It must be understood that, depending on the size and/or shape of the internal chamber, the inlet velocity of the superheated steam injected into the chamber may be adjusted to ensure a desired superheated steam temperature at the outlet of the internal chamber. The non-pregelatinised starch slurry is atomised as it enters the internal chamber and the temperature of said aqueous starch slurry in the atomiser needs to be such that it is sufficiently below the gelatinisation temperature of said starch. The starch slurry preferably has a solids content of from 1 to 40% by weight, more preferably between 10 and 35%, even more preferably of 20 to 35%.

The atomised slurry of starch, which has been only partially gelatinised in the internal chamber of the nozzle, then exits the nozzle through the outlet of the nozzle into a reactor. The slurry, entering the reactor in the form of a spray of droplets containing the partially gelatinised starch, is contacted in the reactor with superheated steam. This further superheated steam treatment of the starch has the result that the starch which was only partially gelatinised in the nozzle becomes completely gelatinised in the reactor.

The reactor may be any reactor used in a spray drying apparatus. Such a spray dryer typically comprises a reactor, at or near the top of which a spray of droplets is introduced and allowed to fall under the influence of gravity. The reactor used in the present invention comprises at least one inlet for the introduction into the reactor of a stream or jet of superheated steam and at least one outlet for allowing the contents of the reactor to exit. Typically, the at least one inlet for the superheated steam in the reactor is positioned such that the stream or jet of superheated steam, after entering the reactor, contacts the droplets containing the partially gelatinised starch at or near to the outlet from the bi-fluid nozzle from which they are discharged into the reactor.

The temperature of the superheated steam introduced into the reactor will be such that it typically has a temperature at the outlet from the reactor in the range of 100° to 165° C., preferably 115° to 140° C. and more preferably from 115° to 125° C.

As mentioned above, according to a preferred embodiment, the superheated steam treatment of the non-pregelatinised starch to produce a partially gelatinised starch which is carried out in the bi-fluid nozzle is carried out in the hi-fluid nozzle of the present invention which is described in detail herein.

The inventors of the present invention have found that by treating non-pregelatinised starches according to the process of the invention, the obtained pregelatinised starches exhibit certain theological and/or viscoelastic properties which are very different from those of starches obtained by prior art methods. For instance, the pregelatinised starches according to the present invention exhibit a much higher cold water viscosity compared to pregelatinised starches prepared by known roll drying or spray cooking/drying methods. This is demonstrated by measuring the apparent viscosity of the pregelatinised starch in UDMSO (9 volumes DMSO, 1 volume 6M urea) at a concentration of 8 mg/ml at 25° C. and the apparent viscosity, under the same conditions, of the corresponding parent non-pregelatinised starch and then calculating the ratio of the apparent viscosity of the pregelatinised starch to the apparent viscosity of the non-pregelatinised starch. The pregelatinised starches obtainable according to the process of the present invention have a ratio (determined as described above) of from 1.00 to 1.18. Accordingly, pregelatinised starches obtainable according to the process of the present invention have high instant viscosity development and achieve viscosities comparable to those of non-pregelatinised starches when gelatinised.

The parameter storage modulus (G') is a measure of the deformation energy stored by a sample during a shear process and is related to the elasticity or stiffness of a gel. The pregelatinised starches obtainable according to the process of the present invention are characterised by a normalised storage modulus G' (c/c*), using a 6% by weight aqueous dispersion of the starch at 30° C., of from 15 to 30 Pa. The present invention, thus, also provides a pregelatinised starch having 1) in UDMSO, (9 volumes DMSO, 1 volume 6M urea) at a concentration of 8 mg/ml at 25° C. ratio of apparent viscosity of said pregelatinised starch to the apparent viscosity of the parent non-pregelatinised starch of from 1.00 to 1.18 at 1 $s^{-1}$; and 2) a normalised storage modulus G' (c/c*) of a 6% by weight aqueous dispersion of the pregelatinised starch at 30° C. of from 15 to 30 Pa.

The storage modulus G' and the viscosity reported herein were measured with a MCR300 rheometer from Anton Paar Physica, Germany, equipped with a cylinder measuring system called starch cell and a shaft ST24 (also from Anton Paar Physica). Further information concerning the storage modulus and viscosity in general can be found in *The Rheology Handbook*, Metzger, T. G. (Vincentz Verlag, Hannover, Germany).

The pregelatinised starch of the present invention wherein the ratio of apparent viscosity of the pregelatinised starch to the apparent viscosity of the parent, non-pregelatinised starch, as described above, is in the range of from 1.00 to 1.18 at 1 $s^{-1}$ and having a normalised storage modulus, as described above, of from 15 to 30 Pa typically contains less than 15% solubles and preferably less than 12% solubles. The starch granule structure of this pregelatinised starch of the present invention is typically not destroyed during the process of its manufacture.

The pregelatinised starch, according to a preferred embodiment, is characterised in that the granules are intact. Furthermore, the pregelatinised starch has a swelling factor, on amylopectin basis (SF(AP)) at 30° C. which is typically from 25 to 40, preferably from 28 to 37 and more preferably from 30 to 35.

According to a further preferred embodiment, the pregelatinised starch of the present invention having 1) in UDMSO, (9 volumes DMSO, 1 volume 6M urea) at a concentration of 8 mg/ml at 25° C. a ratio of apparent viscosity of said pregelatinised starch to the apparent viscosity of the parent non-pregelatinised starch of from 1.00 to 1.18 at 1 $s^{-1}$ and 2) a normalised storage modulus G' (c/c*) of a 6% by weight aqueous dispersion of the pregelatinised starch at 30° C. of from 15 to 30 Pa is characterised further in that the starch granules are intact and that it has a swelling factor, on amylopectin basis (SF(AP)) at 30° C. which is from 25 to 40, preferably from 28 to 37 and more preferably from 30 to 35. Such a pregelatinised starch according to this further preferred embodiment preferably also contains less than 15% solubles, more preferably less than 12% solubles.

The pregelatinised starch according to the present invention has the ability to develop high viscosity when added to aqueous liquids with little or no heating of the aqueous liquid required. Because the starches are pregelatinised, there is no requirement to heat a liquid containing the starch to gelatinisation temperatures in order to develop viscosity. Typically, after a period of 135 seconds starting from the addition of the pregelatinised starch of the invention to an aqueous liquid at 40° C., at 2% by weight concentration, the viscosity attained will be higher than 50 mPa·s, preferably higher than 55 mPa·s and more preferably the viscosity is higher than 60 mPa·s. Typically, the upper limit is between 150 to 200 mPa·s.

According to a yet further preferred embodiment, the pregelatinised starch of the present invention having 1) in UDMSO, (9 volumes DMSO, 1 volume 6M urea) at a concentration of 8 mg/ml at 25° C. a ratio of apparent viscosity of said pregelatinised starch to the apparent viscosity of the parent non-pregelatinised starch of from 1.00 to 1.18 at $1s^{-1}$ and 2) a normalised storage modulus G' (c/c*) of a 6% by weight aqueous dispersion of the pregelatinised starch at 30° C. of from 15 to 30 Pa is characterised further in that the initial viscosity at ($t_o$) 135 seconds is higher than 50 mPa·s, preferably higher than 55 mPa·s, and more preferably higher than 60 mPa·s.

Such a pregelatinised starch according to this yet further preferred embodiment preferably is further characterised in that the granules are intact and that it has a swelling factor on amylopectin basis (SF(AP)) at 30° C. of 25 to 40, preferably from 28 to 37, more preferably from 30 to 35.

A pregelatinised starch according to the yet further preferred embodiment described above preferably is additionally characterised in that it has less than 15% solubles, preferably less than 12% solubles.

A more preferred pregelatinised starch of the invention not only has a ratio of apparent viscosity of the pregelatinised starch to the apparent viscosity of the parent, non-pregelatinised starch, as described above, in the range of from 1.00 to 1.18 at $1s^{-1}$ and a normalised storage modulus, as described above, of from 15 to 30 Pa but also is further characterised in that (a) the granules are intact, in that (b) it has less than 15% solubles, preferably less than 12% solubles, in that (c) it has a swelling factor on amylopectin basis, as described above, at 30° C. of 25 to 40, preferably from 28 to 37 and more preferably from 30 to 35, and in that (d) the initial viscosity at ($t_o$) 135 seconds, as described above, is higher than 50 mPa·s, preferably higher than 55 mPa·s, more preferably higher than 60 mPa·s.

Starches prepared according to the process of the current invention are, due to their high instant viscosity development, suitable in many different applications, in food, in feed, cosmetics, pharmaceutical applications and personal care products. In particular, they are suitable for preparing convenience foods, dairy foods, bakery foods and tablets. Sauces, soups, gravies, puddings, dressings, bakery creams and beverages comprising starches prepared according to the process of the present invention show improved properties in terms of instant viscosity development and dispersibility and, particularly, the Brookfield viscosity in cold liquids is much higher than if other starches are employed. The starches prepared according to the process of the current invention are specifically suitable for use in baby and infant foods. It is crucial in baby and infant food applications that all ingredients have a low microbiological load (amount of microorganisms). The elevated temperatures at which the starch is treated according to the process of the present invention ensure that no microbiological contaminants survive the superheated steam treatment. Furthermore, a closed process, i.e. a process carried out in a system where the starch or flour is not exposed at any time to the environment from the superheated steam treatment to the packaging of the obtained product, ensures that the products will not be contaminated. Therefore, the starches of the present invention can be directly employed in baby and infant foods without the need of any additional treatment.

As stated above, the present invention also provides a bi-fluid nozzle for use in the production of spray dried starch. The bi-fluid nozzle of the invention comprises a nozzle body, a nozzle cap and an internal chamber located between the nozzle body and the nozzle cap, wherein the nozzle body comprises at least one atomiser adapted to be connected to a supply of an aqueous slurry of starch for atomising the aqueous slurry of starch into the internal chamber, wherein the internal chamber has at least one inlet therein adapted to be connected to a supply of superheated steam under pressure for introducing superheated steam under pressure into the internal chamber and wherein the nozzle cap comprises at least one outlet from the internal chamber, wherein the internal chamber also comprises a replaceable and/or interchangeable spacer element with a length of from 4 to 1000 mm, preferably from 4 to 100 mm and more preferably from 4 to 64 mm, most preferably 4 to 15 mm, enabling the length of the internal chamber to be altered. The bi-fluid nozzle has an internal chamber into which, in use, is fed superheated steam under pressure to establish a superheated steam environment inside the internal chamber. An aqueous dispersion or slurry of starch or flour is atomised into the superheated steam environment inside the internal chamber. Atomization of the aqueous dispersion or slurry is carried out by one or more atomisers which are connected to a supply of the dispersion or slurry of the non-pregetatinised starch or flour. The extent of the reaction that takes place between the starch and the superheated steam in the internal chamber depends, inter cilia, on the dimensions of the reaction chamber, particularly on the distance between the atomiser to aperture and the one or more outlets provided in the nozzle cap from which superheated steam and treated starch are discharged from the nozzle. As mentioned above, the internal chamber comprises a replaceable and/or interchangeable spacer element with a length of from 4 to 1000 mm, preferably from 4 to 100 mm and more preferably from 4 to 64 nun, most preferably 4 to 15 mm. This interchangeable spacer element can be replaced by a spacer element having a different length so that the distance between the atomiser aperture and the nozzle cap vent can be altered so as to meet the desired results of the reaction between the starch and the superheated steam. The interchangeable spacer element, therefore, makes possible a pre-selection of the results of the reaction between the starch and the superheated steam. The interchangeable spacer element extends radially inwards into the internal chamber from the side walls of the nozzle. Since the reaction between the starch and the superheated steam is affected by the flow characteristics of the superheated steam in the internal chamber, it is affected by the shape and/or profile of the part or parts of the spacer element which extend inwards into the internal chamber. Thus, the interchangeable spacer element can be pre-selected for use in the nozzle in order to change the flow characteristics in the internal chamber. The interchangeable spacer element may, for instance, be replaced by a different spacer element that constricts the internal chamber or one which has surfaces having configurations or conformations that alter the flow of the superheated steam in the internal chamber, for instance to improve homogeneous distribution of the superheated steam in the internal chamber or to reduce the possibility of heavily turbulent interactions.

The interchangeable spacer element is releasably secured to the nozzle cap and the nozzle body so that it can be replaced easily in the nozzle by an interchangeable spacer element of a different length and/or having different internal shape so as to change the size or shape of the internal chamber. Preferably, the spacer element is annular.

The body of the nozzle will be connected to a liquid feed containing the starch or flour to be subjected to the treatment with superheated steam in the internal chamber. The liquid feed will typically be an aqueous dispersion or an aqueous slurry of the to non-pregelatinised starch or flour and will typically be supplied under pressure, such as by means of a pump, from a holding vessel to the nozzle. The nozzle will, typically, be capable of working under pressurized conditions up to 1,100,000 Pa (11 barg). The internal chamber preferably has a circular cross section. It may be cylindrical, i.e. having a constant diameter.

If only one atomiser is provided by the nozzle body, the aperture of the atomiser is preferably located centrally on the nozzle body. If more than one atomiser is used, the atomisers should, preferably, be arranged symmetrically about the centre of the nozzle body. If only one atomiser is used, the inlet, into the internal chamber, for the superheated steam will preferably be located adjacent to the atomiser. If more than one atomiser is used, the one or more inlets into the internal chamber for the superheated steam will preferably be arranged symmetrically in relation to the atomisers. In a preferred embodiment, the superheated steam is fed into the internal chamber from an annular inlet which surrounds the one or more atomisers.

A preferred embodiment of the bi-fluid nozzle of the present invention which is useful in carrying out the preferred embodiment of the process of the invention is described in detail below with reference to the accompanying FIG. 1.

Figure 1:
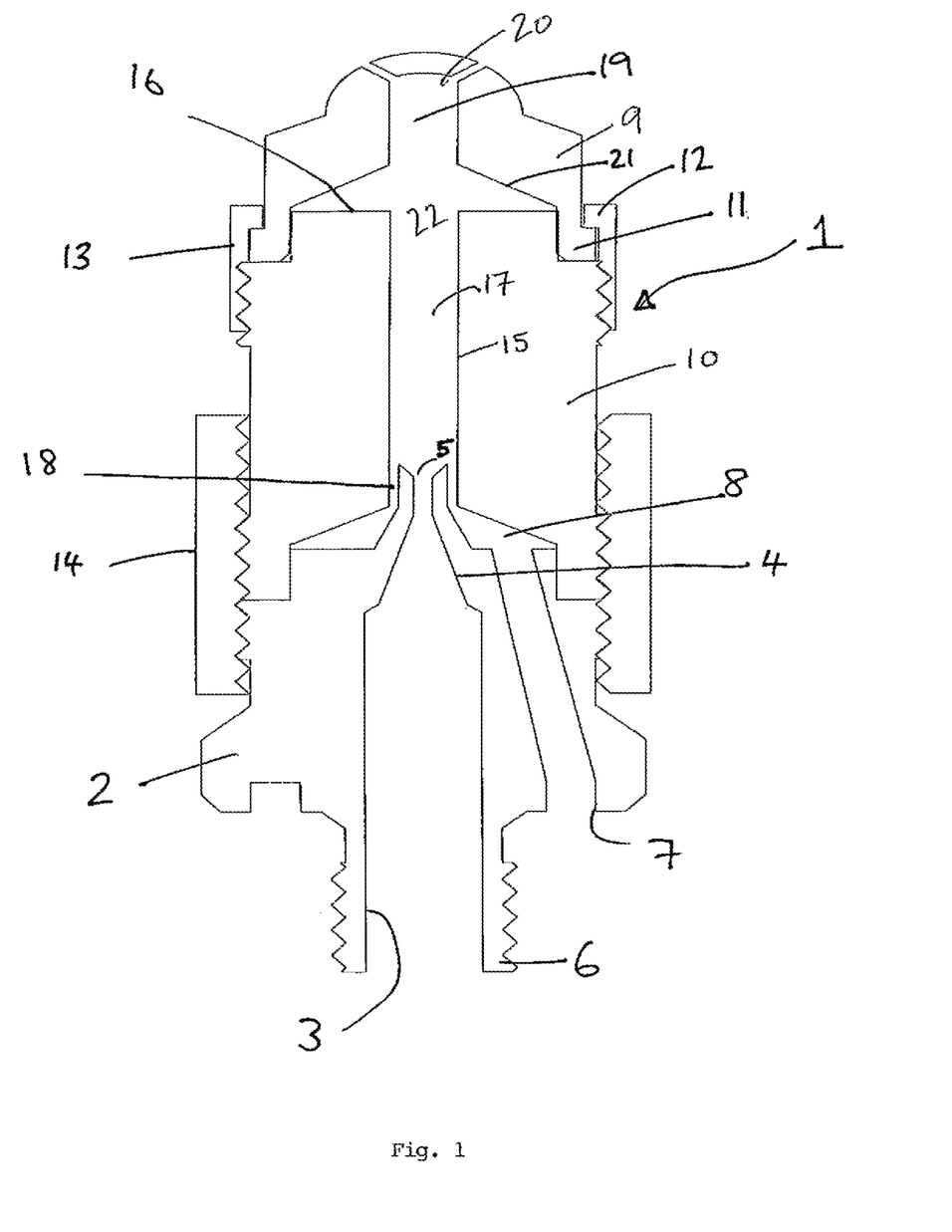
FIG. 1 is a cross-sectional view of a preferred embodiment of the bi-fluid nozzle of the present invention.

FIG. 1 shows a cross-sectional view of one embodiment of a bi-fluid nozzle according to the present invention. The bi-fluid nozzle 1 comprises a nozzle core 2 having a vertically-extending cylindrical bore 3 which, at its uppermost end, extends upwardly and inwardly by a frustoconical section 4 to an atomisation aperture 5. The cylindrical bore 3, at its lowermost end, has a coupling 6 provided with external threads for connection to a supply of an aqueous slurry of starch (not shown). The nozzle core is also provided with a conduit 7 for receiving a flow of superheated steam. The conduit 7, at its uppermost end, opens into an annular chamber 8 surrounding the atomisation aperture 5.

The nozzle 1 has a cap 9 and a replaceable annular spacer element 10. In this embodiment, the cap 9 has an external annular lip 11 which engages with a flange 12 provided on a cylindrical ring 13 having internal threads formed therein which are adapted to engage with external threads formed on the spacer element 10. By the use of the cylindrical ring 13, the cap 9 and the spacer element 10 are releasably secured together. The spacer element is secured to the nozzle body 2 by a cylindrical ring 14 having internal threads formed therein which are adapted to engage with external threads formed on the spacer element and on the nozzle body. The spacer element 10 extends radially inwards towards the aperture 5 and presents an inner surface 15 and an upper surface 16.

The inner surface 15 of the spacer element 10 defines a tubular section 17 which surrounds the atomisation aperture 5 to define an annular channel 18. The nozzle cap 9 has a cylindrical bore 19 which terminates, at its upper end, at a centrally-formed outlet 20 and which terminates, at its lower end, at an inner frustoconical surface 21 which extends downwardly and outwardly from the bore 19 terminating at its lower edge where it meets the upper surface 16 of the spacer element 10.

The enclosed space between the inner surfaces of the nozzle cap 9 and the atomisation aperture 5 forms an internal chamber 22 wherein, in use, the starch is partially gelatinised before it leaves the nozzle via outlet 20. The extent of cooking or gelatinisation of the starch performed in the internal chamber will depend on the distance between the atomisation aperture 5 and the outlet 20 and the volume of the internal chamber. These dimensions of the internal chamber can be changed by replacing the replaceable spacer element 10 by one which has different dimensions, for instance one that defines a tubular section 17 of longer or shorter length and/or one that defines a tubular section 17 of larger or smaller diameter. The spacer element is removed from the nozzle by disengaging it from the nozzle body 2 at the cylindrical ring 14 and is removed from the cap 9 by disengaging it at the cylindrical ring 13. A spacer element having different internal dimensions can then be inserted by re-engaging it with the cap and with the nozzle body.

Thus, the length of, and/or the internal diameter of, the tubular section 17 of the spacer element 10 can be changed as required. The dimensions of the internal chamber, for instance the length of the tubular section 17 defined by the element 10 chosen will depend on the intended function of the final product obtained by the process of the invention and the desired viscosity of the pregelatinised starch when added to cold water. The length of the tubular section, i.e. the length of the spacer element, will be in the range of from 4 to 1000 mm, preferably 4 to 100 mm, more preferably from 4 to 64 mm, most preferably 4 to 15 mm. Typically, the internal diameter of the tubular section 17 will be about 6 mm.

In use, a slurry of ungelatinised starch is supplied under pressure into the bore 3 of the nozzle and is atomised through the aperture 5 into the internal chamber 22 of the nozzle. Superheated steam is fed under pressure into conduit 7 to flow into the annular chamber 8 around the aperture 5. The superheated steam is injected into the spray of atomised starch slurry entering the internal chamber 22 from aperture 5 and the contact of the superheated steam with the sprayed droplets of starch slurry causes the starch in the sprayed droplets to undergo partial but not complete gelatinisation.

The sprayed droplets of partially gelatinised starch exit from or are discharged from the internal chamber via the one or more outlets and are introduced into the reactor where they are subjected to further contact with superheated steam as they fall under the influence of gravity in the reactor. The action of the superheated steam in the reactor on the only partially gelatinised starch in the sprayed droplets introduced into the reactor is that the gelatinisation of the starch in the droplets is completed. As the droplets of starch fall inside the reactor, the water content of the droplets is evaporated off such that the product that can be collected from the bottom of the reactor is in the form of dry, particulate pregelatinised starch.

Preferably, the outlet temperature of the steam or superheated steam leaving the reactor will be in the range of from 100° C. to 165° C., preferably from 115° C. to 140° C., more preferably from 115° to 125° C.

EXAMPLE 1

A slurry (18% by weight dry substance) was formed using waxy maize starch at 25° C. The slurry was fed to a nozzle according to the present invention as illustrated in FIG. 1. The nozzle included a spacer element (10) presenting an inner surface 15 to define a tubular section 17 having an internal diameter of 6 mm. The spacer element had a length of 4 mm.

Before commencing the superheated steam treatment, the internal chamber (22 in FIG. 1) in the nozzle was fitted with a continuous flow of pressurized steam providing heat and velocity in order to get an efficient nebulization of the slurry. The starch slurry was pumped into the nozzle at a flow rate of about 29 litre/hour. The nebulization is done in a continuous superheated steam environment having an inlet temperature of 250°. The atomised slurry, now containing partially gelatinised starch, was discharged into the spray dryer reactor via the outlet in the nozzle and was then subjected to further superheated steam treatment in the reactor. The outlet temperature of the superheated steam leaving the reactor was 137° C. The dried superheated steam-treated starch obtained was collected. A sample of this starch was found to have a swelling factor of 34.6, a normalised storage modulus, G'/(c/c*), of 25 Pa, solubles (w % anhydrous starch) of 10.1 and an apparent viscosity ratio η(outlet)/η(inlet) of 1.15.

Rheology Experiments of Aqueous Starch Pastes:

The tests were carried out on a MCR300 rheometer from Anton Paar Physica, Germany, equipped with a cylinder measuring system called a starch cell and a shaft ST24 (also from Anton Paar Physica). The starch paste was prepared by first measuring the starch moisture content with an IR moisture balance (Sartorius MA30) at 130° C. for 20 minutes. A known amount of starch (see Table 1) is weighed in a 600 ml beaker and wetted with 50 g ethylene glycol. 400 g buffer solution (0.02 M acetate buffer, pH 5.5) was added to the starch and the whole was mixed thoroughly with a large spoon for 1 minute. The paste was then allowed to rest for 1 hour at room temperature before carrying out the measurement.

TABLE 1

| Starch concentration | Starch weight (g, anhydrous basis) | Ethylene glycol (g) | 0.02M acetate buffer pH 5.5 (g) |
|---|---|---|---|
| 6% | 28.9 | 50 | 400 |

Oscillation Test:

The storage modulus G' (Pa) measurements as a function of strain (%) were carried out at 30° C. according to the following procedure.

First interval of 10 minutes: non-recording
Second interval of 600 seconds (10 minutes): recording of data points:
  300 measuring points
  strain 0.1 to 100% log
  frequency 1 Hz Measurement of Starch Swelling and Extent of Solubles Definition of Normalised Storage Modulus Swelling factor The extent of starch swelling was measured at 30° C. using the direct method (100 mg starch) of [Tester and Morrison (1990). Swelling and Gelatinization of Cereal Starches. I. Effects of Amylopectin, Amylose, and Lipids. *Cereal Chemistry* vol. 67, n°6, p. 551-557].

The addition of 5mL 0.02M acetate buffer was performed with a positive displacement pipette under vigorous vortex-mixing to ensure lump-free starch hydration.

The centrifugation is 3,000 g for 10 minutes (instead of 1,500 g for 5 minutes).

The swelling factor SF at 30° C. is a dimensional.

The swelling factor on amylopectin basis SF (AP) at 30° C. is $$SF(AP) = SF \times 100 / AP,$$

where AP is the amylopectin content in weight %.

The amylopectin content (as weight %) is the starch content (as weight %) minus total amylose content (as weight %) determined as its blue value [Morrison and Laignelet (1983). An improved colorimetric procedure for determining apparent and total amylose in cereal and other starches. *Journal of Cereal Science* vol.1, p. 9-20].

Swelling Volume and Close Packing Concentration c*

The swelling factor was converted into a swelling volume q (mL/g) and a close packing concentration c* (g/mL) where c*=1/q, using the method of [Steeneken (1989). Rheological Properties of Aqueous Suspensions of Swollen Starch Granules. *Carbohydrate Polymers* vol. 11, p. 23-41].

The conversion w/w % into w/v % was made assuming the density at 30° C.
  d=0.997 g/mL for 0.02M acetate buffer
  d=1.113 g/mL for ethylene glycol (99.0% by GC)
  d=1.4g/mL for pregelatinised starch Normalised Storage Modulus As described by Steeneken (1989), storage modulus can be expressed as a function of the volume fraction (of swollen starch granules) c/c*=cq.

G'/(c/c*) is the normalised storage modulus

Solubles, i.e. α-Glucan Extractables at 30° C.

A known amount of starch (see Table 2) is weighed in a 600 ml beaker and wetted with 50 g ethylene glycol. 400 g buffer solution (0.02 M acetate buffer, pH 5.5) was added to the starch and the whole was mixed thoroughly with a large spoon for 1 minute. The paste was then stirred (magnetic stirring, 200 min$^{-1}$) for 30 minutes at 30° C.

TABLE 2

| Starch concentration | Starch weight (g, anhydrous basis) | Ethylene glycol (g) | 0.02M acetate buffer pH 5.5 (g) |
|---|---|---|---|
| 1% | 4.5 | 50 | 400 |

The extent of starch solubles was measured from the filtrate (through 0.45 mm) of the supernatant of the starch suspension (after centrifugation at 3,000 g for 10 minutes). The filtrate is hydrolysed with amyloglucosidase and the resulting glucose quantified with glucose oxidase-peroxidase-chromogen as described by [Karkalas (1985). An Improved Enzymic Method for the Determination of Native and Modified Starch. *J. Sci. Food Agric.* vol. 36, p.1019-1027].

All data are reported at 30° C. in 0.02 M acetate buffer pH 5.5.

Solution Properties in UDMSO

The inlet starches (cook-up, i.e. non-pregelatinised) and the outlet starches (SHS, i.e. pregelatinised) of the present invention were dissolved in UDMSO (9 volumes DMSO and 1 volume 6M urea) for 48 hours at room temperature: 800 mg anhydrous starch+100 mL UDMSO.

The apparent viscosity of the solutions was measured on a MCR301 rheometer from Anton Paar Physica, Germany, equipped with a coaxial cylinder double gap measuring system (DG 26.7) and a Peltier temperature device (H-PTD200). The viscosity measurements as a function of shear rate (s$^{-1}$) were carried out at 25° C. according to the following procedure.

First interval of 5 minutes: non-recording
Second interval of 1,650 seconds (27.5 minutes): recording of data points:
  30 measuring points with variable integration time (100 to 10s)
  shear rate 1 to 100s$^{-1}$ When insoluble non α-glucan material is present (e.g. protein in flour), it is recommended to leave the solution undisturbed (1g overnight) or to centrifuge (1,000 g, 10 minutes) prior measurement of apparent viscosity of the supernatant.

The apparent viscosity ratio is the solution viscosity of the outlet starches (SHS, i.e. pregelatinised) in UDMSO divided by the solution viscosity of the inlet starches (cook-up, i.e. non-pregelatinised) in UDMSO at 1 s$^{-1}$ shear rate.

EXAMPLE 2

A slurry (18% by weight dry substance) was formed using waxy maize starch at 25° C. The slurry was fed to a nozzle according to the invention as described above in Example 1 and was treated as described in that Example. Before commencing the superheated steam treatment, the internal chamber in the nozzle was fitted with a continuous flow of pressurized steam providing heat and velocity in order to get an efficient nebulization of the slurry. The starch slurry was pumped into the nozzle at a flow rate of about 29 liter/hour. The nebulization is done in a continuous superheated steam environment having an inlet temperature of 232° C. and an outlet temperature of 137° C. As in Example 1, the temperature of the superheated steam at the outlet of the reactor was 137° C. The dry, pregelatinised starch particles were collected from the bottom of the reactor.

EXAMPLE 3

Figure 2:
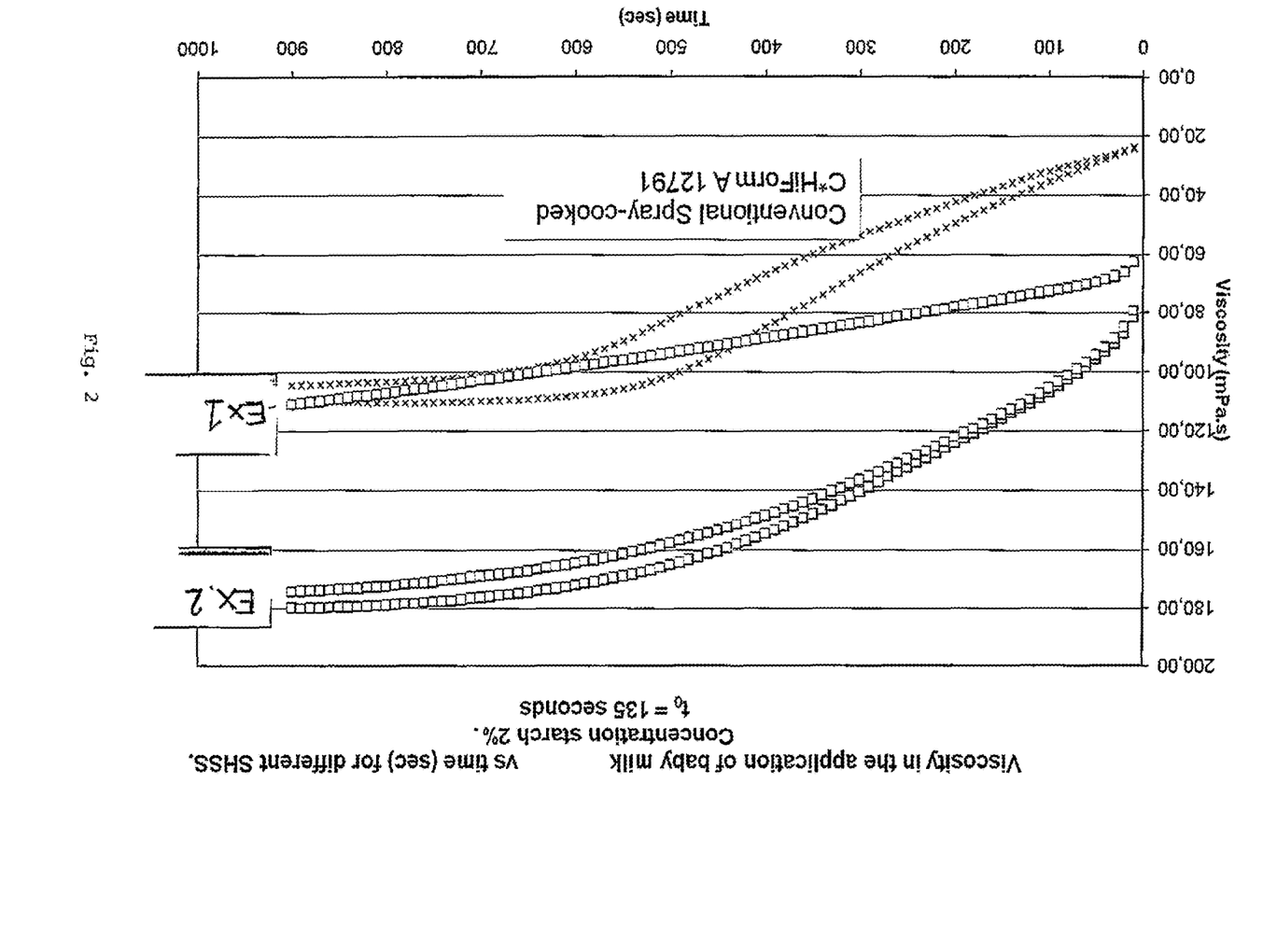
FIG. 2 gives the comparison of the development of viscosity with time for pregelatinised starches produced according to the invention (Examples 1 and 2) and for a conventional spray-cooked starch C*HiForm A 12791 from Cargill, Incorporated.

Baby foods were prepared using the sieved (below 200 μm) starches of Examples 1 and 2, and also using a conventional spray-cooked starch (C*HiForm A 12791 from Cargill, Incorporated). In each case, 3.84 g starch was dry blended with 24.3 g of NAN® Pro baby food mix (starch free). 164 g demineralised water at 40° C. in a bébé-jou baby bottle (250 ml) was conditioned at 40° C. The dry blend was added to the water (time t=0) and shaken for 15 seconds (from t=0 to t=15). The mixture was poured into an Anton Paar Physica MCR 300 starch cell (spindle ST24, 40° C., shear rate 23 s$^{-1}$). The viscosity was measured at exactly t=135 seconds and recorded for 15 minutes with a data integration time of 10 seconds. FIG. 2 shows the development of viscosity in each of the mixtures tested. In FIG. 2, the time 0s on the X-axis corresponds to 135s after the addition of the starch-containing dry mix to the demineralised water. FIG. 2 shows that the starch obtained according to Example 1 developed viscosity more quickly than the conventional spray-cooked starch and that the starch obtained according to Example 2 developed viscosity even more quickly and reaches a final viscosity much higher than that achieved by the other starches.

Comparison of Properties of Product of the Invention (Example 1) with Prior Art

| Properties | Existing product (HiForm A 12791) | WO 2009/013346 | Present Invention (Example 1) |
|---|---|---|---|
| Apparent Viscosity ratio in UDMSO (as described in Example 1) (at 1 s$^{-1}$) | 0.91 | At least 1.05, pref. at least 1.10, more pref. at least 1.15 | 1.15 |
| Normalised storage modulus. (G' (c/c*) at 6% and 30° C. (Pa) (as described in Example 1) | 8 | At least 80, pref. at least 100, more pref. at least 120. | 25 |
| Solubles (W % anhydrous starch) (as described in Example 1) | 16.7 | Less than 15, pref. less than 10, more pref. less than 5 | 10.1 |
| SF (AP) as described in Example 1 | 33.1 | 17.5 | 34.6 |
| Viscosity (mPa · s) as measured according to Example 3 at t$_o$ = 135 seconds | 30.6 | 16.8 | 79.5 |

The invention claimed is:

1. A process for modifying starch comprising the steps:
   a) supplying an aqueous slurry of non-pregelatinised starch to a bi-fluid nozzle of a spray dryer, wherein the hi-fluid nozzle has an internal chamber having at least one inlet for the aqueous slurry of non-pregelatinised starch, at least one inlet for the supply of superheated steam and at least one outlet
   b) atomising the aqueous slurry of non-pregelatinised starch into the internal chamber of the hi-fluid nozzle;
   c) injecting superheated steam into the internal chamber of the bi-fluid nozzle whereby the atomised aqueous slurry of non-pregelatinised starch is heated by the superheated steam in the internal chamber to produce a slurry of partially gelatinised starch, wherein the temperature of the superheated steam at the at least one inlet into the internal chamber is in the range of 150° to 650° C.
   d) discharging the slurry of partially gelatinised starch from the internal chamber through the at least one outlet into a reactor; and
   e) contacting the discharged slurry in the reactor with superheated steam to completely gelatinise the partially gelatinised starch in the discharged slurry and to dry the completely gelatinised starch to produce dry, particulate pregelatinised starch.

2. A process according to claim 1, wherein the non-pregelantised starch in the aqueous slurry of non-pregelatinised starch has an amylose content not greater than 35% by weight.

3. A process according to claim 1, wherein the aqueous slurry of non-pregelatinised starch has a solids content of from 1 to 40% by weight.

4. The process of claim 1, wherein the temperature of the superheated steam at the at least one inlet into the internal chamber is in the range of 250° to 550° C.

5. The process of claim 1, wherein the temperature of the superheated steam at the at least one inlet into the internal chamber is in the range of 350° to 450° C.

6. The process of claim 1, wherein the starch has an amylose content not greater than 10% by weight.

7. The process of claim 1, wherein the non-pregelantised starch in the aqueous slurry of non-pregelatinised starch has an amylose content not greater than 5% by weight.

8. The process according to claim 1, wherein the aqueous slurry of non-pregelatinised starch has a solids content of from 20 to 40% by weight.

* * * * *

UNITED STATES PATENT AND TRADEMARK OFFICE
CERTIFICATE OF CORRECTION

PATENT NO. : 10,239,958 B2  
APPLICATION NO. : 15/254610  
DATED : March 26, 2019  
INVENTOR(S) : Marc Berckmans et al.

Page 1 of 1

It is certified that error appears in the above-identified patent and that said Letters Patent is hereby corrected as shown below:

In the Specification

In Column 2, Line 44, delete "amylase" and insert -- amylose --, therefor.

In Column 2, Line 46, delete "amylase" and insert -- amylose --, therefor.

In Column 2, Line 66, delete "hi-fluid" and insert -- bi-fluid --, therefor.

In Column 4, Line 41, delete "hi-fluid" and insert -- bi-fluid --, therefor.

In Column 4, Line 42, delete "hi-fluid" and insert -- bi-fluid --, therefor.

In Column 5, Line 47, delete "hi-fluid" and insert -- bi-fluid --, therefor.

In the Claims

In Column 14, Line 28, in Claim 1, delete "hi-fluid" and insert -- bi-fluid --, therefor.

In Column 14, Line 33, in Claim 1, delete "hi-fluid" and insert -- bi-fluid --, therefor.

Signed and Sealed this  
Seventeenth Day of September, 2019

Andrei Iancu  
*Director of the United States Patent and Trademark Office*